United States Patent [19]

Chromecek et al.

[11] 4,440,919

[45] Apr. 3, 1984

[54] LOW N-VINYL LACTAM CONTENT BASED BIOMEDICAL DEVICES

[75] Inventors: Richard C. Chromecek, Macedon; Gary D. Friends, Ontario; Lawrence Y. Wissman; Raymond A. Yourd, III, both of Rochester, all of N.Y.

[73] Assignee: Bausch & Lomb Incorporated, Rochester, N.Y.

[21] Appl. No.: 320,353

[22] Filed: Nov. 12, 1981

[51] Int. Cl.$^3$ .................. C08F 226/06; C08F 226/08; G03B 21/46
[52] U.S. Cl. ............................... 526/263; 351/160 R; 351/160 H; 523/108; 526/259; 526/260; 526/262; 526/264; 528/499; 528/500

[58] Field of Search ............... 526/259, 260, 263, 264, 526/262; 528/499, 500; 351/160 R, 160 H

[56] References Cited

U.S. PATENT DOCUMENTS 2,541,152  2/1951  Cairns .................................. 526/263

Primary Examiner—Harry Wong, Jr.
Attorney, Agent, or Firm—Robert M. Phipps; Bernard D. Bogdon

[57] ABSTRACT

Low N-vinyl lactam content copolymers are cross-linked with resonance free di(alkene tertiary amine) cyclic compounds to obtain biomedical devices, including soft contact lenses, which have good oxygen permeability and mechanical properties.

21 Claims, No Drawings

LOW N-VINYL LACTAM CONTENT BASED BIOMEDICAL DEVICES

BACKGROUND OF THE INVENTION

1. Field of the Invention

This invention relates to soft biomedical devices including contact lenses prepared from copolymers containing small amounts of N-vinyl lactam monomers and crosslinked with a resonance free di(alkene tertiary amine) cyclic compound.

2. Prior Art Statement

Many attempts have been undertaken to resolve the problem of polymerization and copolymerization of N-vinyl lactams with the methacrylate type comonomers. An important characteristic of the resulting polymers is their ability to absorb water.

U.S. Pat. No. 3,532,679 (Steckler) describes the polymerization of N-vinyl lactams with alkyl methacrylates such as methyl, ethyl, butyl, 2-hydroxy ethyl, in the presence of a crosslinking agent which is preferably tetraethyleneglycol dimethacrylate. The resulting polymers have water absorption contents of 52% to 95%, however, they can be extracted very easily and lose their original high water content. This reversal of properties is caused by the failure of the dimethacrylates to uniformly copolymerize with the N-vinyl lactam. The hydrogel polymers of this patent are disclosed as suitable for dentistry, surgery, ophthalmology and similar applications.

U.S. Pat. No. 3,700,761 (O'Driscoll et al.) also suggests fabricating contact lens blanks from certain hydrogel compositions obtained from polyvinyl pyrrolidone, a monoester of certain glycols such as hydroxyethyl methacrylate, and no more than about 0.2% by weight of a dimethacrylate. O'Driscoll et al emphasize the extreme importance of selecting the proper constituents and correct relative amounts of each for the fabrication of contact lenses. This criticality of constituents and their relative proportions for fabricating hydrogel contact lenses, which must possess a number of optical and physical characteristics, is discussed in U.S. Pat. No. 3,807,398 (Crucza).

U.S. Pat. No. 3,721,657 (Seiderman) and U.S. Pat. No. 3,792,028 (Seiderman) disclose a copolymer of N-vinyl pyrrolidinone and a hydroxyalkyl methacrylate crosslinked with an alkylene glycol dimethacrylate or methacrylic acid and N-methylolacryl amide. The vinyl pyrrolidinone is present in an amount from 15 to 99 weight percent of the monomer mixture. Examples 6 and 7 show the water content of this type of polymer to be about 40 to above 50 percent. The polymers have optical properties suitable for contact lenses.

U.S. Pat. No. 3,772,235 (Stamberger) discloses using glycidyl methacrylate, glycidyl acrylate or glycidyl crotonate as the crosslinking agent for a heterocyclic N-vinyl monomer such as N-vinyl pyrrolidinone to obtain transparent hydrogels suitable for optical lenses. The polymers thus prepared have water contents ranging from 30% to 70%. Stamberger further discloses in U.S. Pat. No. 3,787,380 the addition of a second comonomer such as methyl methacrylate to obtain a water absorption of 60% to 83%. The polymers are stated to be machinable but no mechanical or oxygen permeability data is presented.

U.S. Pat. No. 3,759,880 (Hoffmann et al.) disclose the preparation of poly-n-vinyl pyrrolidinone-2 by polymerizing vinyl pyrrolidinone in the presence of 0.5 to 10 weight percent of a cyclic acid amide containing at least two ethylenically unsaturated groups and an oxidizable metal. Suitable acid amides include N,N'-divinyl ethylene urea and N,N'-divinyl propylene urea. The resulting insoluble and only slightly swellable polymers are useful for clarifying beer, wine and fruit juices.

U.S. Pat. No. 3,992,562 (Denzinger et al.) and U.S. Pat. No. 4,013,825 (Denzinger et al.) disclose variations of the above Hoffmann et al process in which selected sulfur compounds or ketocarboxycyclic acids or esters are respectively substituted for the oxidizable metal. Another patent to the same assignee, U.K. Pat. No. 1,511,716, discloses the use of similar polymers and copolymers in the field of coatings where divinyl ethylene urea provided better abrasion resistance. None of the examples in these four patents shows the possibility of fabricating an optically clear polymer suitable for contact lens manufacturing nor suggests properties associated with polymers used in such an application.

U.S. Pat. No. 3,949,021 (Kunitomo et al) discloses improving the weak mechanical properties of N-vinyl pyrrolidinone or a combination of N-vinyl pyrrolidinone and other vinyl monomers by simultaneously polymerizing and crosslinking in the presence of soluble linear-polymers such as poly(methyl methacrylate) and monomers such as diallyl phthalate, ethylene glycol diacrylate, hexamethylene bismaleimide, divinyl benzene and divinyl urea. The crosslinking agents having allyl groups are preferred. The resulting polymers have a water absorption of 60% to 90% and are useful for contact lens purposes. Divinyl urea is mentioned among the crosslinking agents, however, it was found that this compound does not polymerize efficiently as suggested by this patent.

U.S. Pat. No. 4,022,754 (Howes et al.) discloses a copolymer of 3-methoxy-2-hydroxypropyl methacrylate (G-MEMA) and N-vinyl lactams crosslinked by a class of di- or multi-functional monomers such as allyl methacrylate or 3-allyloxy-2-hydroxypropyl methacrylate to improve the mechanical strength of the polymer. The copolymers are disclosed as being useful as contact lenses. However, the water content of these copolymers remains low, around 55%. Subsequently, U.S. Pat. No. 4,036,814 (Howes et al) discloses that when the N-vinyl lactam monomer is copolymerized with an aryl or an aryloxy acrylate, or methacrylate or the corresponding amide, a water content of 80% with retention of reasonable mechanical properties can be achieved. The disclosed copolymers include benzyl methacrylate and phenoxyethyl methacrylate. The previously disclosed crosslinking agents are also employed with the new comonomer. Unfortunately, no oxygen permeability data for these polymers is disclosed.

Polymerization of N,N'-divinyl urea was studied by C. G. Overberger at al., *J. Pol. Sci.*, Pt. A-1, vol. 7, 35–46 (1969). It was found that although the divinyl urea exists at room temperature in its vinyl form, the tautomeric form (1)—CO—N=CH—CH$_3$, is formed upon heating. The resulting polymer has the structure

Thermal polymerization of divinyl urea results in soluble (non-crosslinked) polymers. Photo-initiated polymerization of divinyl urea gave similar products. Finally, free radical-initiated polymerization of divinyl urea resulted in insoluble material in lower yield. However, the infrared spectrum and elemental analysis showed all three products to be identical.

U.S. Pat. No. 4,184,992 (Hosaka) summarizes the disadvantages of the prior art N-vinyl lactam base polymers for contact lenses. It was found that those previous art polymers became opaque, distorted upon immersing in boiling water and contained water-soluble extractibles. Hosaka's object was to provide a crosslinking agent reactive with the rest of the monomers to produce a hydrogel having a minimum extractibles and no change in boiling water. The object is more nearly achieved by the use of crosslinking agents with a vinyl or allyl functionality (similar in concept to U.S. Pat. No. 4,036,814) such as vinyl methacrylate, divinyl succinate, triallyl isocyanurate. In the case of polymers having water contents of 68% to 70% the amount of extractibles after 16 hours immersion in boiling water was diminished to between 5% and 10%. In the case of polymers having a water content of 73%, the comparable result was 7% to 9%.

U.S. Pat. No. 4, after N-vinyl pyrrolidinone/alkyl acrylate or methacrylate polymers and compares the properties of these polymers with poly(hydroxymethyl methacrylate) commercially available under the tradename Dura-Soft. Depending on the amount of crosslinking agent, diallyl itaconate, the polymers exhibit water content between 60% and 98% with extractibles of 9% to 20%. The polymer's mechanical strength rating is much inferior to poly(hydroxyethyl methacrylate) which is rated 10, a polymer with a strength rating of 5 has a 57% water content, a polymer with a strength rating of 3 has a 71% water content and a polymer having a strength rating of 3 to 4 has an 80% water content. To achieve low extractibles, 10% or lower at high water content, usually high amounts of crosslinking agent are necessary. The high amount of crosslinking agent causes the formation of rigid polymers having low strength rating. U.S. Pat. No. 4,182,802 (Loshaek et al.) discloses a further attempt to improve the property of this type of polymer by the incorporation of styrene as a comonomer. Again, as long as the amount of crosslinking agent is low, higher extractibles, 10% to 18% resulted.

From the foregoing, it can be appreciated that there is still a need for an optically clear polymer of N-vinyl lactam which has low extractibles, good mechanical properties (especially the tear strength), oxygen permeability and good machinability for use in various biomedical applications.

SUMMARY OF THE INVENTION

In accordance with this invention, N-vinyl lactam/hydrophilic monomer crosslinked copolymer for biomedical applications characterized by oxygen permeability and water absorption is improved by the use of a resonance free di-(alkene tertiary amine) cyclic compound as the crosslinking agent of said copolymer whereby improved tear strength, good machinability, low extractibles and oxygen permeability are obtained. The obtained copolymers are clear and suitable for biomedical applications, including extended wear contact lenses, heart valves and films. More particularly, the invention concerns soft contact lenses for extended wear purposes.

DESCRIPTION OF THE PREFERRED EMBODIMENTS

The monomers employed in accordance with this invention are readily polymerized to form 3-dimensional polymeric networks which permit the transport of oxygen and are optically clear, strong and soft. The term "soft" is used in the well established sense of the contact lens field to describe polymeric products which are either flexible or semiflexible.

The nitrogen containing monomer used in the preparation of the copolymers of this invention is conveniently referred to as an N-vinyl lactam which includes (a) N-vinyl lactams per se and (b) other heterocyclic N-vinyl monomers. Illustrative of the N-vinyl lactams that are employed in this invention are: N-vinyl-2-pyrrolidinone, N-(1-methyl vinyl) pyrrolidinone, N-vinyl-2-piperidone and N-vinyl-2-caprolactam which may be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone and N-vinyl-6-methyl piperidone. Illustrative of the other heterocyclic N-vinyl monomers used in preparing the copolymers of this invention are: N-vinyl imidazole, N-vinyl succinimide, N-vinyl diglycolylimide, N-vinyl glutarimide, N-vinyl-3-morpholinone and N-vinyl-5-methyl-3-morpholinone. The lactam may be an admixture of two or more lactam monomers to give hydrogels having the particularly desired characteristics. The preferred monomer is N-vinyl-2-pyrrolidinone.

The N-vinyl lactam monomer(s) are used in conjunction with one or more hereinafter defined hydrophilic comonomers. The n-vinyl lactam will constitute less than 50% of the copolymer and more preferably from 15% to 40% by weight of the total monomers employed. More than one hydrophilic comonomer may be admixed with the N-vinyl lactam. The preferred amount of N-vinyl lactam in the polymer composition is 15 to 40 percent by weight to achieve a water content of 40 percent or more. The percent water is calculated as follows:

$$\text{Percent Water} = \frac{\text{Wet Weight} - \text{Dry Weight}}{\text{Wet Weight}} \times 100$$

The hydrophilic comonomer of this invention is an ester, free acid, amide or an amine of acrylic acid, methacrylic acid or itaconic acid. The hydrophilic monomer(s) constitute at least 50 percent of the total amount of monomers employed in preparing the copolymers of this invention.

Illustrative of suitable hydrophilic comonomers are the mono-, di-, tri-, tetra- and poly-ethylene glycol monoacrylates or methacrylates or itaconates as well as the acids per se. Hydroxyalkyl methacrylates with 1 to 6 carbon atoms in the alkyl group are within the scope of this invention. Useful amides of the foregoing acids include acryl, methacryl, N-mono- or di-substituted diacetone acrylamide. Also useful are the amines of the foregoing acids such as mono- or di-alkylamino substituents. The preferred hydrophilic monomers are glycol methacrylates, particularly hydroxyethyl methacrylate (HEMA).

It is within the scope of this invention that other hydrophilic comonomers within the above class and disclosed by the prior art can be advantageously used within the scope of this invention.

The advantageous compositions of this invention are obtained by the incorporation therein of a resonance free di(alkene tertiary amine) cyclic compound as a crosslinker. The crosslinkers can be simplistically visualized as of the formula $CH_2{:}CG(CH_2)_xN{\sim}J{\sim}N(CH_2)_xCG{:}CH_2$ wherein x is 0 or 1, G is hydrogen or methyl and the J group is the balance of a structure forming a cyclic dialkene urea, a dialkene hydrazide, dialkene amide, dialkene hydantoin, dialkene hydrouracil or a dialkene 2,2′-bisimidazolin. The alkene group in the cyclic compounds of this invention is either vinyl (when x is 0) or allyl (when x is 1) and G is hydrogen, or alpha methyl vinyl or alpha methyl allyl when G is methyl. Illustrative of cyclic dialkene ureas useful in this invention are N,N′-divinyl ethylene urea (also known as N,N′-divinyl imidazolid-2-one) having the formula

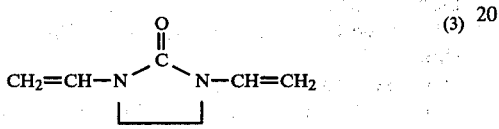
(3)

the corresponding N,N′-diallyl ethylene urea and N,N′-di(alpha methyl vinyl) ethylene urea, N,N′-diallyl propylene urea and the corresponding N,N′-di(alpha methyl allyl) propylene urea and N,N′-divinyl propylene urea (also known as N,N′-divinyl hexahydropyrimidine-2-one) having the formula

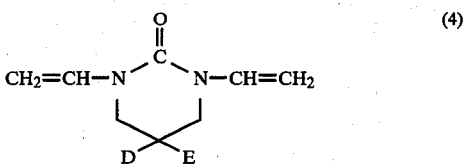
(4)

wherein D and E are each independently selected from the group consisting of hydrogen or alkyl of 1 to 12 carbon atoms and preferably 1 to 6 carbon atoms. In the foregoing formula (4) when both D and E are hydrogen, the compound is the forementioned N,N′-divinyl propylene urea. Still other useful cyclic di(alkene ureas) are compounds such as those having the structural formulas shown in formulas (5), (6) and (7) below wherein x in each case is 0 or 1 and G is hydrogen or methyl,

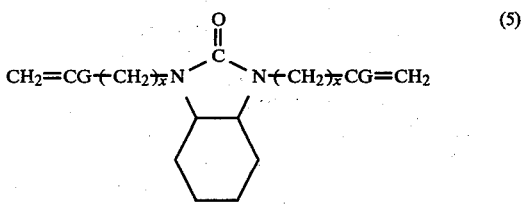
(5)

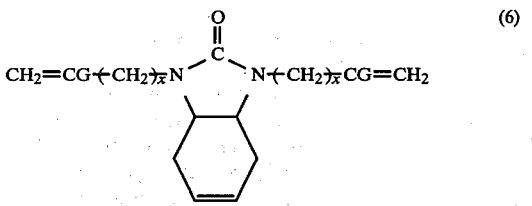
(6)

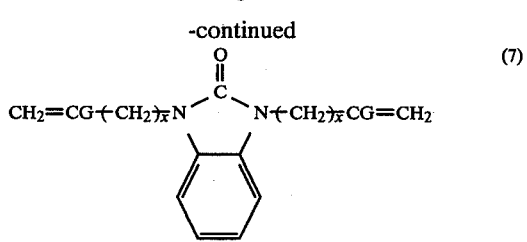
(7)

Illustrative of the di(alkene amides) useful as crosslinking agents in the present invention are compounds having chemical structures represented by the formulas (8) and (9) below,

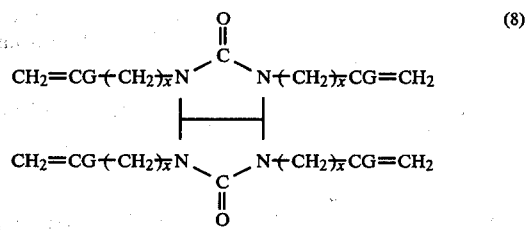
(8)

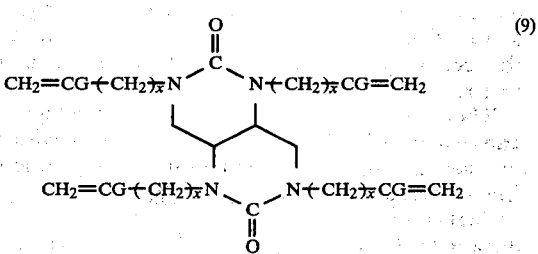
(9)

Illustrative of the di(alkene)hydrazides useful as crosslinking agents in the present invention are compounds having chemical structures illustrated by formulas (10) and (11) below,

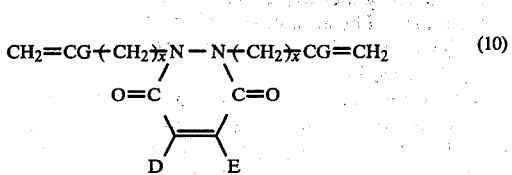
(10)

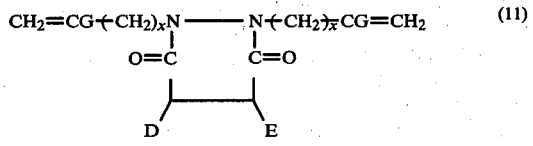
(11)

The di(alkene) hydantoins useful as crosslinking agents in this invention have the general formula,

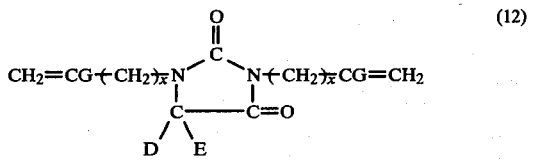
(12)

Illustrative of the di(alkene) hydrouracils suitable as a crosslinking agent of this invention are those shown in formulas (13) and (14) below,

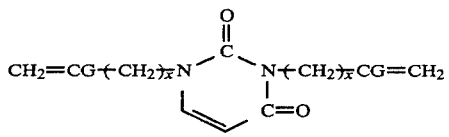

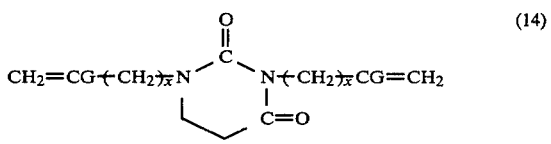

Finally, illustrative of the di(alkene) 2,2'-bis imidazolin useful as a crosslinking agent in the present invention is 1,1'-diallyl-2,2'-bis-imidazolin and the corresponding 1,1'-divinyl-2,2'-bis-imidazolin which has the formula

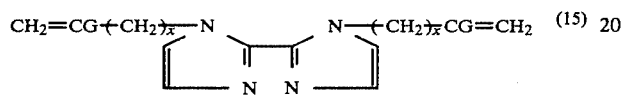

In formulas 4, 10, 11 and 12 above, D is hydrogen or alkyl of $C_1$–$C_{12}$, preferably $C_1$–$C_6$; E is hydrogen or alkyl of $C_1$–$C_{12}$, preferably $C_1$–$C_6$. In formulas 5 through 15 inclusive above, G is hydrogen or methyl and x is 0 or 1.

The foregoing di(alkene tertiary amine) compounds can be used either singularly or in combination with one another in obtaining the desired crosslinking structure of the polymers of this invention. The di(alkene tertiary amine) compound is present in an amount from 0.01 to 10 weight percent and preferably from 0.1 to about 3.0 percent.

The N-vinyl lactam hydrophilic monomer mixture of this invention when mixed with the resonance free di(alkene tertiary amine)cyclic compound crosslinking agent with or without optional additional crosslinking agents are generally clear, colorless liquids of varying viscosity. These monomer mixtures can be readily cured to cast shapes by conventional methods such as free radical initiation.

The free radical type initiators suitable for this invention include peroxides, azo compounds, UV initiation, oxidation-reduction systems and similar initiators described in the literature. Illustrative of free radical initiators which can be employed are bis(isopropyl) peroxy dicarbonate, 2,2'-azobis[isobutyronitrile], acetyl peroxide, benzoin methyl ether, lauroyl peroxide, decanoyl peroxide, benzoyl peroxide, 2,2'-azobis[2,4-dimethylvaleronitrile], tertiarybutyl peroctoate, phthalic peroxide, cumene hydroperoxide, diethoxyacetophenone, tertiary butyl peroxypivalate.

As is well known in the contact lens art, water soluble diluents may be used with the foregoing polymers to modify the physical properties of these polymers. More particularly, the diluents may be advantageous in improving machinability and swell characteristics of the polymer. Typically, the amount of diluent will be less than 50 weight percent of the total monomers employed and preferably not more than 30 weight percent.

In a particular polymer system, the limiting amount of diluent is the solubility of the diluent in the monomer system. Thus, there should be no phase separation between diluent and starting monomer mixture. Additionally, excessive amounts of diluent will result in collapse of the cell structure of the finished biomedical devices when the device is hydrated, i.e., replacement of diluent by water.

The maximum amount of diluent is readily ascertained by swelling the diluent free polymer in the proposed diluent and measuring the degree of swell. Comparable results are obtained when using solvent soluble diluents wherein the solvent does not affect the lens polymer. These solvents include ketones, e.g., methyl ethyl ketone and isopropyl alcohol.

Suitable diluents include ethylene glycol, glycerine, liquid polyethylene glycols, butanol, butanol/water mixtures, ethylene oxide/propylene oxide block copolymers having a molecular weight from 1,000 to 5,000, low molecular weight, e.g., 500 to 10,000, linear poly(vinyl pyrrolidinone), low molecular weight linear poly(hydroxyethyl methacrylate), glycol esters of lactic acid, formamide, dimethyl formamide, methyl ethyl ketone, dimethyl sulfoxide and the like. In the finished biomedical device, it will be necessary to replace any diluent with an aqueous solution. The contact lens should, of course, contain a physiological saline solution as the aqueous medium.

The polymers of this invention can be formed into medical surgical devices and contact lenses by methods well known in the prior art. By way of example, mixture of the desired N-vinyl lactam, hydrophilic monomer, free radical type initiator, the di(alkene tertiary amine) cyclic compound crosslinking agent and any optional crosslinker or monomer described above is purged with an inert gas such as nitrogen or carbon dioxide and filled into polypropylene tubes having dimensions of 18 mm × 300 mm. The polymerization is then carried out by gradually heating from 30° C. to 110° C. in a step fashion over a span of several days. In a typical long schedule the tubes are placed in a water bath from 30° C. to 50° C. for two to three days followed by two days at 60° C. The rod is then removed from the mold and post-cured at 110° C. for a period up to about four hours. A typical short schedule is disclosed in U.S. Pat. No. 3,721,657 (Seiderman). The fully cured rods are then cut into cylinders, optionally then annealed at temperatures up to 150° C., and machined to form contact lenses as desired. Other conventional methods such as compression molding as disclosed in U.S. Pat. Nos. 4,084,459 and 4,197,266 or spincasting process as described in U.S. Pat. Nos. 3,408,429 and 3,496,254 can be employed to prepare useful objects of this invention.

The contact lenses made from the polymer of the instant invention are oxygen permeable. A critical oxygen tension and flux under a lens should be about 10 mmHg and 2 ml/(cm$^2$hr.) respectively below which corneal swelling occurs, see Polse and Decker, *Investigative Ophthalmology and Visual Science*, Vol. 18, p 188, 1979. In order to meet these requirements, the lens material must have adequate oxygen permeability. These more preferred contact lenses have an oxygen permeability of at least about $8 \times 10^{-11}$ cm$^3$cm/(sec.cm$^2$mmHg), are hydrolytically stable, biologically inert and transparent. The most preferred contact lenses have an oxygen permeability of at least $10 \times 10^{-11}$. In comparison, the well-known contact lens polymer poly(hydroxyethyl methacrylate), hereafter referred to as PHEMA, has an oxygen permeability value of about $8 \times 10^{-11}$ cm$^3$cm/(sec.cm$^2$mmHg).

Additionally, these lenses are hydrolytically stable meaning that when the contact lenses are placed into an aqueous solution, e.g., on the eye, or during disinfecting step, i.e., water plus heat, the lenses will not change in chemical composition, i.e., hydrolyze. On heating in boiling water for 120 hours, the typical polymer of this invention experiences a water content loss of 3 percent or less.

Thus, the copolymers disclosed herein can be boiled and/or autoclaved in water without being damaged whereby sterilization may be achieved. An article formed from the disclosed copolymers may be used in surgery where an article compatible with living tissue or with the mucous membranes may be used.

The copolymers of this invention being soft yet resilient and hard to tear are well suited for use in biomedical devices, including contact lenses. It is well known that the wearer of soft contact lenses will have an unavoidable amount of handling of the lenses. Part of the cleaning and rinsing procedure is to rub each lens and tearing has been a concern in prior art lenses. The copolymers of the present invention have a tear initiation strength (ASTM D-1938) of at least 2 g/mm of thickness and preferably 2 g/mm or more.

These polymers can also be used in preparing medical surgical devices, e.g., heart valves, vessel substitutes, intrauterine devices, membranes and other films, dialyzer diaphragms, catheters, mouth guards, denture liners and other such devices as disclosed in Shephard U.S. Pat. Nos. 3,618,231 and 3,520,949. The instant polymers can be used to modify collagen to make blood vessels, urinary bladders and other such devices as disclosed in Kliment, U.S. Pat. No. 3,563,925. Also, these polymers can be used to make catheters as disclosed in Shephard, U.S. Pat. No. 3,566,874. These polymers can be used as semi-permeable sheets for dialysis, artificial dentures and all of such disclosures as set forth in Stoy, U.S. Pat. No. 3,607,848.

The terms "shaped article for use in biomedical applications" or "biomedical devices" mean the materials disclosed herein have physicochemical properties rendering them suitable for prolonged contact with living tissue, blood and the mucous membranes. These properties are required for biomedical shaped articles such as surgical implants, blood dialysis devices, blood vessels, artificial ureters, artificial breast tissue and membranes intended to come in contact with body fluid outside of the body, e.g., membranes for kidney dialysis and heart-/lung machines and the like. It is known that blood, for example, is rapidly damaged in contact with artificial surfaces. The design of a synthetic surface which is antithrombogenic and nonhemolytic to blood is necessary for prostheses and devices used with blood. The polymers and copolymers are compatible with living tissue.

The following examples are illustrative only and should not be construed as limiting the invention. All parts and percents referred to herein are on a weight basis. Temperature is expressed in degrees Celsius unless otherwise specified.

EXAMPLE I

A series of copolymers are prepared using a comonomer mixture consisting of 80% 2-hydroxyethyl methacrylate (HEMA) and 20% N-vinyl-2-pyrrolidinone (NVP). The crosslinker, and amount employed for each composition, is indicated in the Table below. The polymerization is initiated by the addition of 0.05 percent tertiary butyl peroctoate. The solution is cast between glass plates separated by a Teflon ® (DuPont registered trademark) perfluoro polymer gasket of 0.3 mm thickness. The film is cured to 15 hours at 60° C., then one hour at 80° C. and finally one hour at 100° C. In each instance, clear homogeneous films are obtained. The resulting films are evaluated.

For convenience, hereinafter the divinyl ethylene urea crosslinker of this invention will be referred to as DVEU and the crosslinking agent of the prior art, ethylene glycol dimethacrylate, will be referred to as EGDMA.

To avoid differences in the interpretation of the oxygen permeability determination, poly(hydroxyethyl methacrylate) hydrogel (PHEMA) was used as a control. The oxygen permeability is expressed as a ratio of the permeability of the copolymer/permeability of PHEMA. A typical oxygen permeability value for PHEMA hydrogel: $8.0 \times 10^{-11}$ cm$^3$ cm/(sec.cm$^2$ mmHg). The oxygen permeability measurements were made using a flat polarographic sensor. The method used was basically that described by Refojo, M., Holly, F., and Leong, F-L., *Contact and Intraocular Lens Medical Journal*, Vol. 3, Issue 4, p 27, (1977). The determinations are carried out on samples having a thickness of about 0.3 mm. The values are corrected for sample thickness. The results are tabulated in Table I below. As seen from the results, oxygen permeability of the polymer of this invention with DVEU crosslinking agent is higher than the copolymers utilizing the prior art crosslinking agent, EGDMA.

Tear strength is a very important property in considering polymeric compositions for soft contact lenses. It is well known that the wearer of soft contact lenses, following prescribed procedures, will have an unavoidable amount of handling of the lenses each day. The results in Table I below show that the polymers according to this invention (A,B,C,D) have superior elongation and tear properties compared to the prior art compounds (E,F,G,H). Not only are higher values for each level of crosslinker achieved, but over the full range, the compounds of this invention exhibit less fall off in the respective property. Additionally, the oxygen permeability property, a critical value for contact lenses, remains constant in contrast to the declining values of the prior art compounds.

EXAMPLE II

To a mixture containing 20 g of N-vinyl pyrrolidinone, 80 g of hydroxyethyl methacrylate monomers and 0.05 g tertiary butyl peroctoate polymerization initiator is admixed 0.1 g of the crosslinking agent, DVEU. The solution is purged with nitrogen for 10 minutes and then poured into polypropylene tubes having a diameter of 18 mm and a length of 300 mm. The tubes are closed and vented and then immersed in a constant temperature water bath and heated to 60° C. for 16 hours. Then the tubes are placed in an oven and maintained at 143° C. for ½ hour. Cylinders (or buttons) are cut from the rod and annealed by heating to 143° C. in an oven for ½ hour. From the cylinders, contact lenses are machined. The resulting lenses are suitable for optical use.

EXAMPLE III

The procedure of Example I is repeated except that 0.3 g of DVEU are added. The resulting lenses are also suitable for optical use.

TABLE I

| COMPOSITION | AMOUNT CROSS-LINKER (PERCENT) | MODULUS$^a$ (g/mm$^2$) | TENSILE (g/mm$^2$) | ULTIMATE ELONGATION (PERCENT) | TEAR$^b$ (g/mm$^2$) INITIAL | TEAR$^b$ (g/mm$^2$) PROPOGATION | OXYGEN PERMEABILITY (X PHEMA) | WATER (PERCENT) | WATER EXTRACTIBLES$^c$ (PERCENT)$^d$ |
|---|---|---|---|---|---|---|---|---|---|
| | | | | DVEU CROSSLINKER (This Invention) | | | | | |
| A | 0.3 | 58.0 | 66.7 | 211.8 | 3.49 | 2.18 | 1.3 | 47.3 | 7.1 |
| B | 0.6 | 60.4 | 72.2 | 212.0 | 3.39 | 2.09 | 1.3 | 47.1 | 5.8 |
| C | 1.2 | 64.8 | 63.9 | 172.7 | 2.87 | 1.87 | 1.3 | 46.7 | 6.6 |
| D | 2.0 | 81.4 | 72.3 | 138.4 | 2.48 | 1.81 | 1.3 | 45.5 | 5.3 |
| | | | | EGDMA CROSSLINKER (Prior Art) | | | | | |
| E | 0.3 | 67.3 | 87.4 | 208.4 | 2.86 | 1.98 | 1.3 | 45.9 | 5.9 |
| F | 0.6 | 84.9 | 64.9 | 114.0 | 2.00 | 1.42 | 1.2 | 45.2 | 6.6 |
| G | 1.2 | 114.0 | 66.5 | 76.4 | 1.99 | 1.43 | 1.1 | 41.7 | 4.7 |
| H | 2.0 | 152.0 | 80.8 | 63.9 | 1.81 | 1.48 | 0.98 | 41.7 | 5.9 |

$^a$Tangent modulus of elasticity, tensile strength and elongation were determined following ASTM D-1708 procedure.
$^b$Tear initiation and tear propogation were determined following ASTM D-1938 procedure.
$^c$Boiled in water for one-half hour.
$^d$Percent extractibles = $\frac{\text{Original dry weight} - \text{Extracted dry weight}}{\text{Original dry weight}} \times 100$

EXAM

A casting solution is prepared by mixing together 80 parts of 2-hydroxypropyl methacrylate, 20 parts of N-vinyl-2-caprolactam, 1 part of N,N'-divinyl propylene urea and 0.2 parts of 2,2'-azobis(isobutyronitrile). A clear homogeneous film suitable for optical purposes is prepared when the solution is cast and cured according to the procedure of Example I.

EXAMPLE V

A casting solution is prepared by mixing together 75 parts of 2-dimethylaminoethyl methacrylate, 25 parts of N-vinyl-3-morpholinone, 1 part of N,N'-divinyl-2,2-dimethyl propylene urea and 2 parts of 2,2'-azobis (isobutyronitrile). The mixed, degassed solution is placed in a suitable contact lens spincasting mold. It is spincast with ultraviolet radiation for one-half hour and then post cured for one hour at 80° C. to obtain the desired lens. The lens is optically clear, oxygen permeable, flexible and strong.

EXAMPLE VI

A casting solution is prepared by mixing together 65 parts of methacrylamide, 25 parts of N-vinyl glutarimide, 10 parts diethyleneglycol monoacrylate, 1 part of 1,1'-diallyl-2,2'-bis-imidazolin and 2 parts of 2,2'-azobis (isobutyronitrile). Following the procedure of Example V, useful contact lenses are obtained by the spincasting method.

EXAMPLE VII

Example III is repeated except that 15 parts of ethylene glycol are added to the monomer mixture. After fabrication of contact lenses from the buttons, the lenses are extracted in hot water for ½ hour to remove the extractibles and then equilibrated in physiological saline.

The preceding examples and methods have been described in the foregoing specification for the purpose of illustration and not limitation. Other modifications and ramifications will naturally suggest themselves to those skilled in the art based on the disclosure. These are intended to be comprehended as within the scope of this invention.

The embodiments of the invention in which an exclusive property or privilege is claimed are defined as follows:

1. As a new article of manufacture a contact lens formed from a hydrophilic polymer formed by polymerizing (a) one or more N-vinyl lactams and/or heterocyclic N-vinyl monomers, said N-vinyl lactams being selected from the group consisting of N-vinyl-2-pyrrolidinone, N-(1-methyl) vinyl pyrrolidinone, N-vinyl-2-piperidone and N-vinyl-2-caprolactam which may be substituted in the lactam ring by one or more lower alkyl groups, said heterocyclic N-vinyl monomers being selected from the group consisting of N-vinyl imidazole, N-vinyl succinimide, N-vinyl diglycolylimide, N-vinyl glutarimide, N-vinyl-3-morpholinone and N-vinyl-5-methyl-3-morpholinone, (b) one or more hydrophilic comonomers selected from the group consisting of hydroxyesters, free acids, amides and amines of acrylates, methacrylates, or itaconates, said hydrophilic monomer(s) being at least 50% of the total monomer of (a) and (b) present and (c) a resonance free di(alkene tertiary amine) cyclic crosslinking agent, said cyclic compound having the formula $CH_2:CG(CH_2)_xN \sim J \sim N (CH_2)_xCG:CH_2$ wherein x is 0 or 1, G is hydrogen or methyl and J is the balance of a structure forming cyclic dialkene urea, said agent being present in an amount from 0.01 to 10 weight percent of the total monomers of (a) and (b) present to form a crosslinked 3-dimensional polymeric network, said polymer having an oxygen permeability of at least $8 \times 10^{-11}$ cm$^2$ cm/sec.cm$^2$ mmHg) and a tear initiation strength of at least 2 g/mm of thickness.

2. The article according to claim 1 wherein the resonance free di(alkene tertiary amine) cyclic compound is selected from the group consisting of cyclic dialkene urea, dialkene amides, dialkene hydrazides, dialkene hydantoins, dialkene hydrouracils, dialkene 2,2'-bis-imidazolin and mixtures thereof, said alkene being either vinyl, alpha methyl vinyl, alpha methyl allyl or allyl.

3. The article according to claim 1 wherein the resonance free di(alkene tertiary amine) cyclic compound is a cyclic divinyl urea.

4. The article according to claim 3 wherein the cyclic divinyl urea is divinyl ethylene urea.

5. The article according to claim 2 wherein the cyclic compound is a dialkene 2,2'-bis-imidazolin.

6. The article according to claim 5 wherein the dialkene 2,2'-bis-imidazolin is 1,1'-divinyl-2,2'-bis-imidazolin.

7. The article according to claim 5 wherein the 2,2'-bis-imidazolin is 1,1'-diallyl-2,2'-bis-imidazolin.

8. The article according to claim 2 wherein the resonance free di(alkene tertiary amine) cyclic compound is a cyclic allyl urea.

9. The article according to claim 8 wherein the cyclic allyl urea is diallyl ethylene urea.

10. The article according to claim 1 wherein the crosslinking agent is present in an amount from 0.1 to 3.0 weight percent.

11. The article according to claim 1 wherein the N-vinyl lactam and/or heterocyclic N-vinyl monomer is an N-vinyl lactam.

12. The article according to claim 11 wherein the N-vinyl lactam is N-vinyl-2-pyrrolidinone.

13. The article according to claim 11 wherein the N-vinyl lactam is N-vinyl-2-caprolactam.

14. The article according to claim 1 wherein the N-vinyl lactam and/or heterocyclic N-vinyl monomer is a heterocyclic N-vinyl monomer.

15. The article according to claim 14 wherein the heterocyclic N-vinyl monomer is N-vinyl-5-methyl-3-morpholinone.

16. The article according to claim 14 wherein the heterocyclic N-vinyl monomer is N-vinyl glutarimide.

17. The article according to claim 1 wherein from 15% to 40% by weight of the total monomers employed is the N-vinyl lactam or a mixture of the N-vinyl lactams and from 60% to 85% by weight is the hydrophilic comonomer or a mixture of the hydrophilic comonomers.

18. The article according to claim 17 wherein the N-vinyl lactam is N-vinyl pyrrolidinone and the hydrophilic comonomer is hydroxyethyl methacrylate.

19. The article according to claim 17 wherein the N-vinyl lactam is N-vinyl pyrrolidinone and the hydrophilic comonomer is hydroxypropyl methacrylate.

20. A process for preparing the article of claim 1 comprising (a) admixing together the monomers and crosslinking agent with a free radical initiator, (b) charging the mixture to a mold and (c) activating and maintaining the activation of the free radical initiator until the desired degree of crosslinking has been obtained.

21. The process of claim 20 wherein a water soluble or solvent soluble diluent is admixed with the monomer and crosslinking agent and after the article has been formed removing the diluent by washing the article with water.

* * * * *